US009555254B2

(12) United States Patent
Benecke et al.

(10) Patent No.: US 9,555,254 B2
(45) Date of Patent: Jan. 31, 2017

(54) IMPLANTABLE MEDICAL DEVICE WITH COMMUNICATION BY WAY OF PHYSICAL CONNECTOR, SYSTEM AND METHOD THEREFORE

(75) Inventors: Walter E. Benecke, Scottsdale, AZ (US); Lonny Cabelka, Chandler, AZ (US); Mark A. Maass, Tempe, AZ (US); Melvin P. Roberts, Chandler, AZ (US)

(73) Assignee: Medtronic, Inc., Minneapolis, MN (US)

( * ) Notice: Subject to any disclaimer, the term of this patent is extended or adjusted under 35 U.S.C. 154(b) by 32 days.

(21) Appl. No.: 13/472,211

(22) Filed: May 15, 2012

(65) Prior Publication Data

US 2013/0211470 A1 Aug. 15, 2013

Related U.S. Application Data

(60) Provisional application No. 61/598,622, filed on Feb. 14, 2012.

(51) Int. Cl.
*A61N 1/00* (2006.01)
*A61N 1/372* (2006.01)
*A61N 1/378* (2006.01)
*A61N 1/08* (2006.01)

(52) U.S. Cl.
CPC ............ *A61N 1/37217* (2013.01); *A61N 1/08* (2013.01); *A61N 1/3787* (2013.01); *A61N 1/37211* (2013.01); *A61N 1/37252* (2013.01)

(58) Field of Classification Search
CPC ............ A61N 1/37217; A61N 1/37252; A61N 1/37211; A61N 1/3787; A61N 1/08

USPC .................................. 607/1, 2, 32, 33, 60
See application file for complete search history.

(56) References Cited

U.S. PATENT DOCUMENTS

| 4,106,494 A * | 8/1978 | McEachern .......... A61N 1/3931 600/508 |
| 4,989,602 A | 2/1991 | Sholder et al. |
| 7,013,178 B2 | 3/2006 | Reinke et al. |
| 7,493,174 B2 | 2/2009 | Belalcazar et al. |
| 7,724,148 B2 * | 5/2010 | Samuelsson et al. ..... 340/573.1 |
| 2002/0147473 A1 * | 10/2002 | Seim et al. .................... 607/14 |
| 2005/0283203 A1 * | 12/2005 | Flaherty et al. ............... 607/48 |
| 2006/0149330 A1 | 7/2006 | Mann et al. |
| 2006/0265540 A1 | 11/2006 | Mass et al. |
| 2007/0100384 A1 | 5/2007 | Fischell et al. |
| 2009/0062880 A1 | 3/2009 | Li et al. |

(Continued)

FOREIGN PATENT DOCUMENTS

WO WO 2005/032656 A1 4/2005

*Primary Examiner* — Niketa Patel
*Assistant Examiner* — Lindsey G Hankins

(57) ABSTRACT

System, implantable medical device and method for communicating between an implantable medical device and an external communication device. The implantable medical device has a physical connector, a medical module and a communication module. The medical module is configured to at least one of deliver a therapeutic output by way of the physical connector and/or sense data indicative of a physiologic condition of a patient by way of the physical connector. The external communication device is configured to communicate with the communication module by way of the physical connector. In an embodiment, electronic communication may be by way of a differential pair of connectors.

28 Claims, 4 Drawing Sheets

(56) References Cited

U.S. PATENT DOCUMENTS

2009/0088812 A1    4/2009  Wulfman et al.
2009/0275849 A1   11/2009  Stewart
2010/0312298 A1*  12/2010  Pontiga et al. .................. 607/9
2011/0022113 A1    1/2011  Zdeblick et al.

* cited by examiner

IMPLANTABLE MEDICAL DEVICE WITH COMMUNICATION BY WAY OF PHYSICAL CONNECTOR, SYSTEM AND METHOD THEREFORE

This application claims priority from U.S. Provisional Application No. 61/598,622, filed on Feb. 14, 2012, entitled "IMPLANTABLE MEDICAL DEVICE WITH COMMUNICATION BY WAY OF PHYSICAL CONNECTOR, SYSTEM AND METHOD THEREFORE."

FIELD

The present invention relates generally to implantable medical devices, systems and method therefore, and, more particularly, to communications with such implantable medical devices, systems and method therefore.

BACKGROUND

Implantable medical devices such as pacemakers, defibrillators and neurological stimulators treat various patient conditions through the delivery of electrical stimulation to the patient by way of electrodes operatively coupled to device circuitry by way of a connector block. The electrodes are operatively coupled to a power source and electronics which control delivery of therapeutic stimulation. The electrodes are then placed in proximity of patient tissue to which electrical stimulation is to be delivered. It is commonly the case that at least some electrodes are positioned on leads to be placed in proximity of the target patient tissue and which couple to the implantable medical device by way of the connector block.

Because such implantable medical devices are advantageously and commonly physically isolated under the cutaneous boundary of the patient with respect to external devices, such implantable medical devices typically utilize wireless telemetry to communicate with users by way of external devices. Because such implantable medical devices are physically isolated, they typically incorporate batteries to supply device power. However, such batteries are commonly either non-rechargeable or only rechargeable through inconvenient methods. As a result, implantable medical devices are typically configured to consume as little power as practical, including for telemetry. Consequently, telemetry is typically configured to transmit at relatively low data rates over relatively short ranges; inductive communications have historically served such purposes, while more recently low-power, short range radio frequency communication schemes have started to become more common.

When implanted, implantable medical devices are often configured to transmit and receive amounts of data that are very small in comparison with other common devices which transmit data, such as computers, cellular telephones and the like. As a result, implantable medical devices may not necessarily accumulate and save as much data as they might in theory be able to collect because transmitting out such data may be impractical given the limitations of the telemetry system.

After an implantable medical device has been manufactured and programmed, it may not be practical to transmit data to the implantable medical device by way of the telemetry system. However, during manufacture, all or most of the functionality of various aspects of the implantable medical device may need to be communicated to the implantable medical device. Similarly, in order to significantly analyze a condition or status of an implantable medical device after the device has been used and explanted from a patient, a significant amount of data may be need to be transferred. Consequently, a wireless communication system configured to facilitate relatively small amounts of data transfer over a given time may require large amounts of time to receive enough information to substantially program an implantable medical device or comprehensively analyze a condition of an implantable medical device. As a result, manufacturing processes and device analyses may be lengthened undesirably by a need to wait for extended periods while wireless communication of programming instructions occurs. Such delays may lengthen manufacturing time and analysis time and thereby increase costs.

SUMMARY

A system has been developed which provides for transfer of data to and from a medical device than may be realized by conventional wireless communication schemes in medical devices. In particular, the implantable medical device may be configured to communicate by way of the connector block and, in certain embodiments, the electrodes. In various embodiments, the implantable medical device may be configured to transmit information by way of the electrical contacts of the connector block to which the electrodes couple; a second connector which is configured to interface with the contacts of the connector block may thereby provide for electrical coupling to the electronics of the implantable medical device, permitting direct and relatively rapid communication.

Even when the implantable medical device is configured with electrodes and leads, the electrodes and leads may still provide coupling to the connector block and from there to the electronics of the implantable medical device. By utilizing the conductive properties of the patient's tissue, relatively low-voltage signals may be transmitted to and from the electrodes at essentially no measureable impact to the patient tissue using tissue conductive communications. Consequently, though a direct connection to the connector block may not be achievable, communication may still occur through the connector block.

It is the case, however, that implantable medical devices may be relatively isolated from conventional ground or reference voltages. In other words, due to isolation which may be desirable to insulate implantable medical devices from outside influences, implantable medical devices may not utilize a reference voltage which is accessible by an outside device. Because direct electronic communications typically occur relative to a common reference voltage, direct communication may be made impractical without a provided reference. Consequently, the implantable medical device may utilize a differential pair of conductors, which may provide a floating ground over which communications may occur.

In an embodiment, a medical system comprises an implantable medical device and an external communication device. The implantable medical device comprises a physical connector, a medical module configured to at least one of (1) deliver a therapeutic output by way of the physical connector and (2) sense data indicative of a physiologic condition of a patient by way of the physical connector, and a communication module. The external communication device is configured to communicate with the communication module by way of the physical connector.

In an embodiment, the physical connector comprises a differential pair of connectors and wherein the communication module is configured to at least one of transmit and receive electronic communication differentially via the differential pair of connectors.

In an embodiment, the physical connector comprises a floating ground.

In an embodiment, the communication through the communication module comprises at least one of a command to control an operation of the implantable medical device and data relating to a condition of the implantable medical device.

In an embodiment, the communication through the communication module comprises a command to control an operation of the implantable medical device.

In an embodiment, the communication through the communication module comprises a wakeup command and electronic data, and the implantable medical device is configured, upon receiving the wakeup command, to disable a functionality of the medical block prior to receiving the electronic data.

In an embodiment, when the implantable medical device has been implanted in a patient having a heart with periodic beats, the implantable medical device is configured to disable the functionality of the medical block during a time between consecutive ones of the periodic beats, and the external communication device is configured to communicate during the time between consecutive ones of the periodic beats.

In an embodiment, the implantable medical device is configured to sense physiologic signals from the patient, the physiologic signals occurring in discrete time periods, and the implantable medical device is configured such that communication through the communication module occurs only at a time other than the discrete time periods in which the physiologic signals are sensed by the implantable medical device.

In an embodiment, the discrete time periods comprise times of periodic heart beats and wherein the implantable medical device is configured such that the communication through the communication module occurs only outside of the times of periodic hearts beats.

In an embodiment, the implantable medical device further comprises a telemetry module configured to wirelessly communicate with the external communication module.

In an embodiment, the patient has patient tissue and wherein the external communication device is further configured to communicate with the communication module by way of patient tissue of a patient and the physical connector.

In an embodiment, the external communication device is configured to be physically coupled to the physical connector using at least one of a direct connection, a resistive connection and a capacitive connection.

In an embodiment, the implantable medical device further comprises a case containing the medical module and the communication module, and wherein the external communication device is configured to communicate with the communication module by way of the physical connector and the case.

In an embodiment, an implantable medical device comprises a physical connector, a medical module and a communication module. The medical module is configured to at least one of (1) deliver a therapeutic output by way of the physical connector and (2) sense data indicative of a physiologic condition of a patient by way of the physical connector. The communication module is configured to communicate with an external communication device by way of the physical connector.

In an embodiment, a method of operating an implantable medical device having a physical connector comprises the steps of performing at least one of (1) delivering a therapeutic output by way of the physical connector and (2) sensing data indicative of a physiologic condition of a patient by way of the physical connector, and electronically communicating with the implantable medical device by way of the physical connector.

In an embodiment, the physical connector comprises a differential pair of connectors and the communicating step comprises communicating differentially via the differential pair of connectors.

In an embodiment, the communicating step comprises communicating with a floating ground.

In an embodiment, the communicating step comprises at least one of a command to control an operation of the implantable medical device and data relating to a condition of the implantable medical device.

In an embodiment, the communicating step comprises a command to control an operation of the implantable medical device.

In an embodiment, the method further comprises the step of sending a wakeup command to the implantable medical device to disable a functionality of the medical block prior to receiving the electronic data.

In an embodiment, the communicating step occurs during a time between consecutive ones of periodic beats of a heart of the patient.

In an embodiment, the communicating step occurs only at a time other than in discrete time periods in which physiologic signals are sensed by the implantable medical device.

In an embodiment, the method further comprises the step of wirelessly communicating with the external communication module.

In an embodiment, the communicating step occurs by way of patient tissue of a patient and the physical connector.

In an embodiment, the communicating step occurs with the external device being physically coupled to the physical connector using at least one of a direct connection, a resistive connection and a capacitive connection.

In an embodiment, the communicating step occurs by way of the physical connector and the case.

FIGURES

DESCRIPTION

The entire content of provisional U.S. Provisional Application Ser. No. 61/598,622, filed Feb. 14, 2012, is hereby incorporated by reference.

Figure 1:
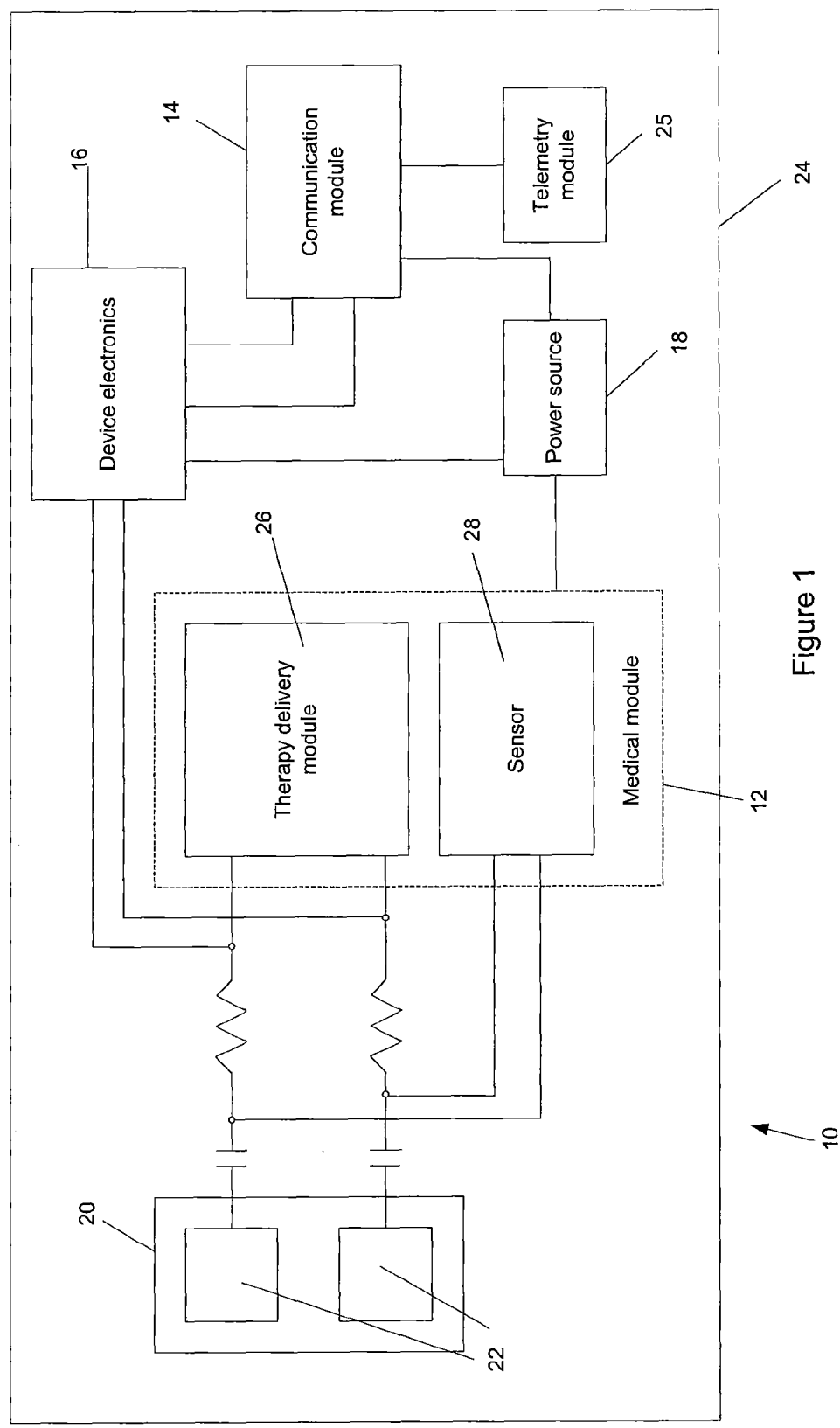
FIG. 1 is a block diagram of an implantable medical device.

FIG. 1 is a block diagram of implantable medical device 10. In various embodiments, implantable medical device is one of various implantable medical devices well known in the art, including pacemakers, defibrillators, neurological stimulators and the like. As is common among such implantable medical devices 10, implantable medical device 10 incorporates medical module 12, communication module 14, device electronics 16 and power source 18, such as a battery or other power sources known in the art. Various such components are available off-the-shelf, while others are proprietary designs as appropriate.

Implantable medical device further incorporates physical connector block 20 having, in the illustrated embodiment, two (2) electrode contacts 22. In various embodiments described below, contacts 22 form a differential pair of contacts 22. In various embodiments, implantable medical device 10 incorporates more than two (2) contacts 22, in certain embodiments thirty-two (32) or more contacts 22. In various embodiments, implantable medical device incorporates one (1) contact 22 and is configured to use housing 24, which is configured to hermetically-seal implantable medical device 10, as an electrode.

Communication module 14 is configured to receive and transmit communications by way of device electronics 16 and contacts 22, or by way of telemetry module 25. Telemetry module 25 is configured to communicate via methods other than those provided by way of contacts 22, such as by inductive communications or radio frequency transmissions. In such embodiments, communication module 14 formats communications for transmittal by either device electronics 16 or telemetry module 25, as appropriate. Communication module 14 is configured to receive commands to control an operation of implantable medical device 10, including therapy delivery and sensing function of medical module 12. In addition, communication module 14 is configured to generate data relating to a condition of implantable medical device 10 for transmission by way of contacts 22.

As illustrated in FIG. 1, medical module 12 comprises therapy delivery module 26 and sensor block 28. In various embodiments, medical module 12 incorporates one but not both of therapy delivery module 26 and sensor block 28, either rendering implantable medical device 10 capable of delivering therapy but not sensing or reacting to a patient condition, or of sensing a patient condition, such as a physiologic condition, but not treating the patient. In the various embodiments of implantable medical device 10, therapy delivery module 26 is configured to deliver electrical stimulation to patient tissue via electrodes operatively coupled to contacts 22 or via housing 24, as appropriate. Such therapy may include, but not be limited to, cardiac pacing, cardioversion, cardiac defibrillation, neurological stimulation, and other electrical therapy as known in and according to the art.

Sensor block 28 variously includes sensors configured to sense changes in electric potential between electrodes coupled to contacts 22 and housing 24, as appropriate. Such sensors may be configured to deliver a small stimulation pulse, in comparison with the therapy delivered by therapy delivery module 26, and note a change in a received signal. Such sensors may further be configured to detect electrocardiograms and neurological activity, among other functions known in the art. It is noted that various implantable medical devices 10 which incorporate sensors in sensor block 28 which are sensitive to changes in electric potential may also incorporate sensors which do not sense variations in electric potential. Such sensors may include blood pressure sensors and blood oxygen sensors, among others known in the art. Such sensors may be incorporated as components of sensor block 28.

Figure 2:
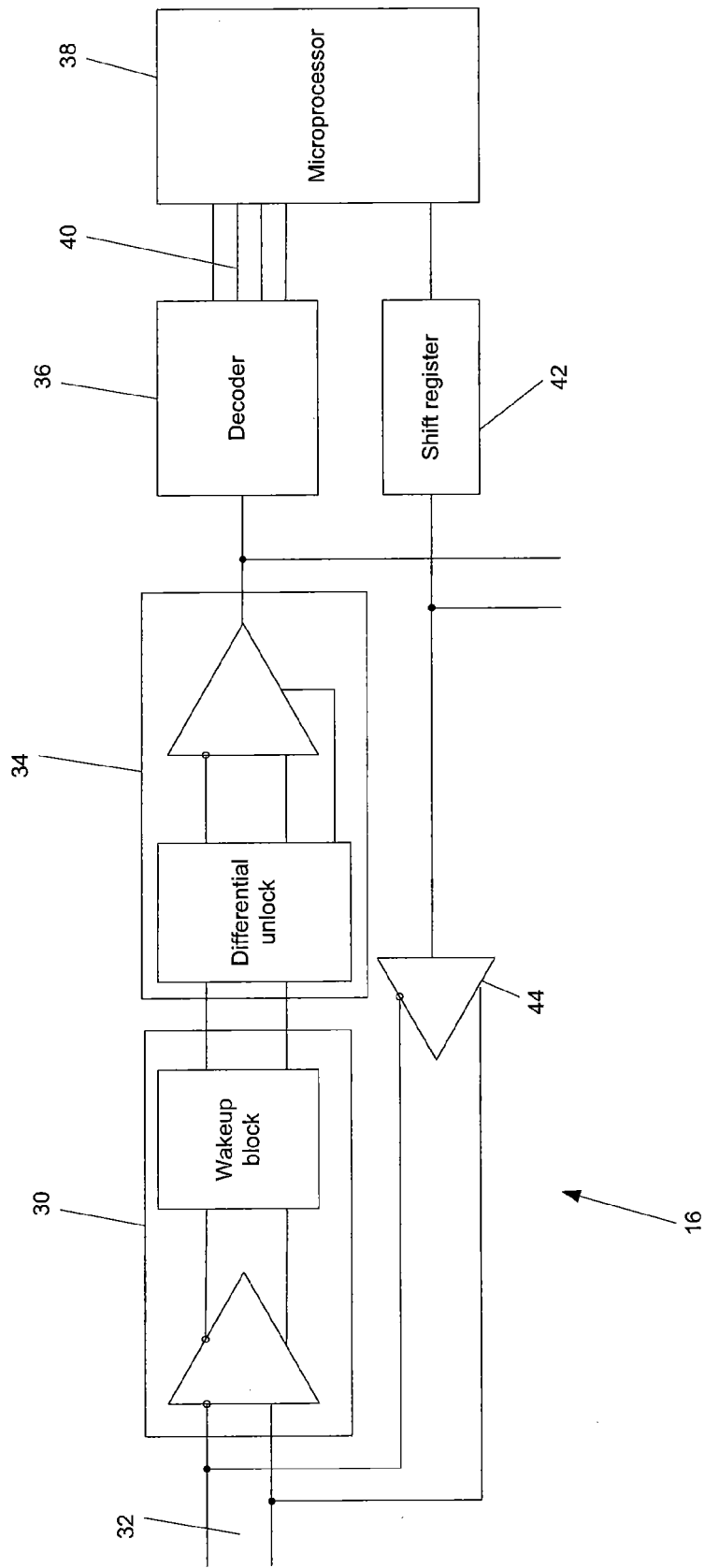
FIG. 2 is a block diagram of a portion of electronics of the implantable medical device of FIG. 1.

FIG. 2 is a block diagram of at least some componentry of device electronics 16. Wakeup block 30 is configured to detect a wakeup condition from differential input line 32 which is ultimately coupled to contacts 22 as illustrated in FIG. 1. An output of wakeup block 30 may be utilized to enable other componentry of implantable medical device 10 on the basis of a transmitted wakeup signal or binary burst detected by wakeup block 30. In various embodiments, wakeup block 30 is configured to disable at least one of therapy delivery module 26 or medical module 12 in general to prevent interference with incoming communication signals by delivered therapy. In various embodiments, wakeup block 30 is not utilized and the circuitry of implantable medical device 10 either operates without using a wakeup condition, or a wakeup signal is transmitted to a different block in implantable medical device 10.

As illustrated, two-channel differential input 32 is a floating ground differential data channel. In alternative embodiments, two-channel differential input 32 may have more than two channels. Actual connection differential input 32 to contacts 22 is, in various embodiments, via direct connect, resistive connect and capacitive coupled connection, and may be selectable on the basis of required data speed and safety expectations, as known in the art. In an exemplary embodiment where implantable medical device 10 is a pacemaker or cardioverter/defibrillator, direct connections may be made between a ventricular tip electrode and housing 24. In an exemplary embodiment where implantable medical device 10 is a neurological stimulator, any two active electrodes are utilized.

Differential unlock 34 is configured to unlock electronic circuit functionality based on a transmitted unlock code or device identifier, and then to convert the differential signal of differential input line 32 into a conventional signal which utilizes a common reference of implantable medical device 10. Such differential unlocking is performed according to methods well known in the art. The input for differential unlock 34 is an output of wakeup block 30, which is, in various embodiments, a substantially unattenuated pass-through signal from differential input 32. Differential unlock 34 may be regulated, at least in part, by a timer from wakeup block 30. In an embodiment, the timer is one second in duration, after which differential unlock 34 again locks or inhibits the differential conversion and transmittal of received signals until another wakeup condition has been detected by wakeup block 30.

In various embodiments, a standard communication protocol, a hybrid protocol or a custom protocol may be utilized once the differential unlock 34 is unlocked and a communication channel has been established. Such communication protocols are variably serial or parallel. Standard communication protocols supported include, but are not limited to, serial protocol interfaces, an inter-integrated circuit or "I$^2$C" protocol, a joint test action group or "JTAG" architecture according to the IEEE 1149.1 standard, a compact joint test action group or "cJTAG" architecture according to the IEEE 1149.7 standard, and tissue conductive communications as described above. In various embodiments, the version of the IEEE 1149.1 standard promulgated in 1990 is utilized. In various alternative embodiments, any IEEE 1149.1 or 1149.7 standards may be utilized, including those not yet promulgated at the time of this writing.

Decoder 36 is configured to decode instructions in the signal as unlocked by differential unlock 34. The decoded instructions are provided to microprocessor 38 by way of input lines 40. Decoder 36 and microprocessor 38 are configured according to methods well known in the art and are, in various embodiments, standard off-the-shelf components or proprietary components. Shift register 42 is configured to stage the output of microprocessor 38, as controlled by instructions provided by decoder 36. The input and output from decoder 36, microprocessor 38 and shift register 42 may be regulated by instructions from differential unlock, in an embodiment by toggling an enable switch.

In an embodiment, decoder 36 is configured to convert received instructions and data into boundary scan instruction register and data register commands and data. Decoder 36 is configured to generate boundary scan signals based on the IEEE 1149.1 standard. In various embodiments, decoder 36 is configured to generate test signals, such as a test clock signal, a test mode select signal, a test data in command and a test data out command. In various embodiments, such test signals are utilized during a manufacturing test of implantable medical device 10.

Data transmittal from device electronics 16 is differential based on a conversion by differential converter 44. In various embodiments, data is transmitted differentially through contacts 22. In such embodiments, communications generated by microprocessor, whether output test data from a manufacturing test or device operational information during device 10 operation, are converted to a differential signal and output through contacts 22. Alternatively, in various embodiments, unique differential output connectors may be utilized for output signals while contacts 22 are dedicated to input signals.

Figure 3:
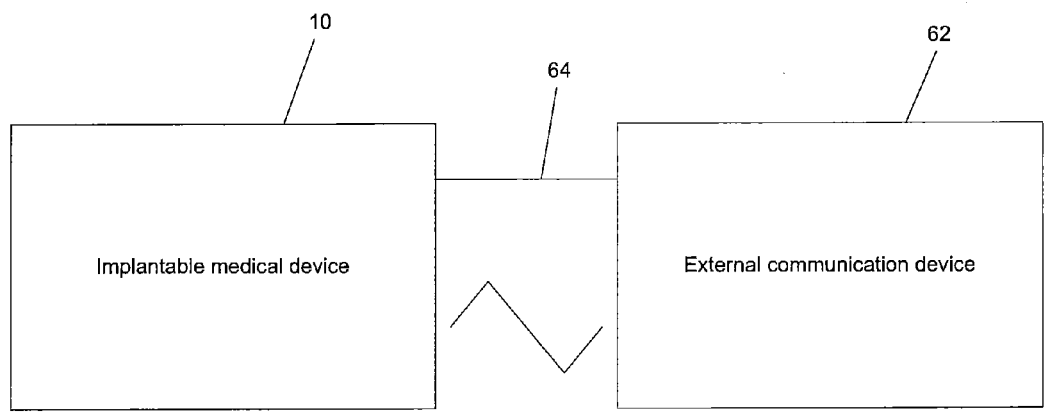
FIG. 3 is a block diagram of a system incorporating the implantable medical device of FIG. 1.

FIG. 3 is a diagram of system 60 which incorporates implantable medical device 10 and external communication device 62. In the illustrated embodiment, external communication device 62 is directly coupled to contacts 22 of implantable medical device 10 with cable 64, over which external communication device 62 communicates with implantable medical device 10 as described in detail above. In various alternative embodiments, including those in which implantable medical device 10 is implanted in a patient, external communication device 62 is configured to communicate with implantable medical device 10 by way of tissue conductive communications. In such embodiments, differential, electrically stimulative communication signals are transmitted through patient tissue and are detected by contacts 22.

In embodiments in which implantable medical device is implanted in a patient, therapy delivery may interfere with tissue conductive communications. In such embodiments, stimulative therapy from therapy delivery module 26 of medical module 12 may overwhelm the tissue conductive communications. In addition, in embodiments where implantable medical device is, for instance, a pacemaker, a beat by the heart of the patient may also interfere with tissue conductive communications. Consequently, in an embodiment, as discussed above, medical module 12 or components thereof may be disabled during tissue conductive communications, i.e., for a time following a wakeup signal detected by wakeup block 30. In an embodiment, external communication device 62 is configured not to transmit via tissue conductive communications during a periodic cardiac beat. Similarly, external communication device 62 may be configured to synchronize with a physiologic signal from the patient, such as the heart beat, so that communications occur other than during or only outside of discrete time periods in which the physiologic signals are detectable by sensor block 28 of implantable medical device 10.

In various embodiments, implantable medical device 10 may utilize either contacts 22 or telemetry module 25 to communicate with external communication device 62. Whichever method of communication is utilized may be selectable as appropriate. In various embodiments, and under various circumstances, communication block 14 may switch between communication through contacts 22 and telemetry module 25 based on factors such as current or anticipated therapy delivery or physiologic signal detection.

Figure 4:
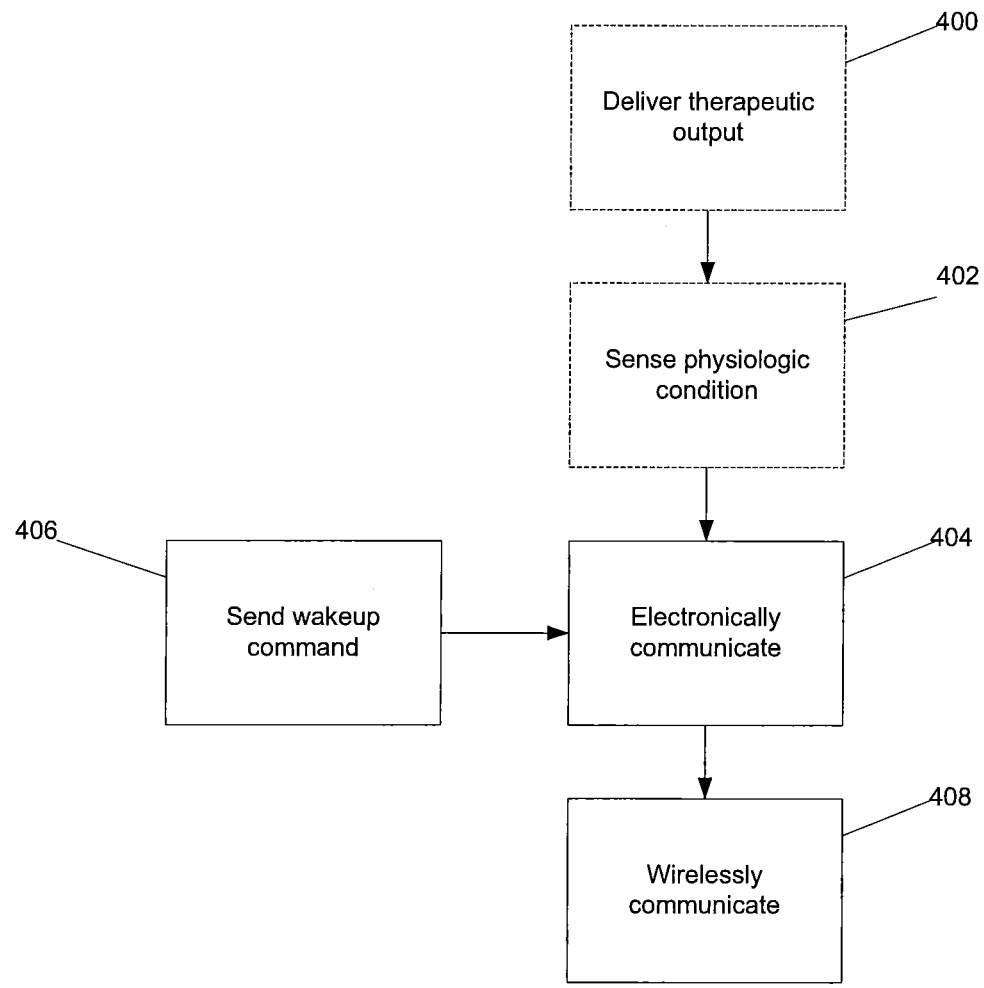
FIG. 4 is a method for operating the implantable medical device of FIG. 1 and the system of FIG. 3.

FIG. 4 is a flowchart of a method for operating implantable medical device 10. Implantable medical device 10 utilizes therapy delivery module 26 to deliver (400) a therapeutic output and/or utilizes sensor block 28 to sense (402) data indicative of a physiologic condition of a patient. Communication block 14 utilizes device electronics 16 to electronically communicate (404) with external communication device 62 by way of contacts 22 of physical connector 20. Electronic communications may follow a wakeup command sent (406) by way of contacts 22 and received by wakeup block 30. External communication device 62 and implantable medical device 10 may wirelessly communicate (408) with communication module 14 utilizing telemetry module 25.

Thus, embodiments of an implantable medical device configured to communicate with an external communicative device by way of a physical connector and method are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A medical system, comprising:
   an implantable medical device, comprising:
   a physical connector having a plurality of contacts;
   a medical module configured to at least one of (1) deliver a therapeutic output through specific ones of said plurality of contacts of said physical connector and (2) sense data indicative of a physiologic condition of a patient through said specific ones of said plurality of contacts of said physical connector; and
   a communication module configured to communicate through said specific ones of said plurality of contacts of said physical connector; and
   an external communication device configured to communicate with said communication module through said specific ones of said plurality of contacts of said physical connector;
   wherein said communication through said communication module comprises a wakeup command and electronic data; and
   wherein said implantable medical device is configured, upon receiving said wakeup command, to unlock functionality of said implantable medical device and to disable a functionality of said medical module to prevent interference between said communication using said electronic data and said data indicative of said physiologic condition.

2. The system as in claim 1 wherein said specific ones of said plurality of contacts comprise a differential pair of contacts and wherein said communication module is configured to at least one of transmit and receive electronic communication differentially through said differential pair of contacts.

3. The system as in claim 2 wherein said physical connector comprises a floating ground.

4. The system as in claim 1 wherein said communication through said communication module comprises at least one of a command to control an operation of said implantable medical device and data relating to a condition of said implantable medical device.

5. The system as in claim 4 wherein said communication through said communication module comprises a command to control an operation of said implantable medical device.

6. The system as in claim 1 wherein when said implantable medical device has been implanted in a patient having a heart with periodic beats, said implantable medical device is configured to disable said functionality of said medical module during a time between consecutive ones of said periodic beats; and
wherein said external communication device is configured to communicate only during said time between consecutive ones of said periodic beats.

7. The system as in claim 1:
wherein said implantable medical device is configured to sense physiologic signals from said patient, said physiologic signals occurring in discrete time periods;
wherein said implantable medical device is configured such that communication through said communication module occurs only at a time other than said discrete time periods in which said physiologic signals are sensed by said implantable medical device.

8. The system as in claim 7 wherein said discrete time periods comprise times of periodic heart beats and wherein said implantable medical device is configured such that said communication through said communication module occurs only outside of said times of periodic hearts beats.

9. The system as in claim 1 wherein said external communication device is configured to be physically coupled to said specific ones of said plurality of contacts of said physical connector using at least one of a direct connection, a resistive connection and a capacitive connection.

10. The system as in claim 1 wherein said implantable medical device further comprises a case containing said medical module and said communication module, and wherein said external communication device is configured to communicate with said communication module through said plurality of contacts of said physical connector and said case.

11. An implantable medical device, comprising:
a physical connector having a plurality of contacts;
a medical module configured to at least one of (1) deliver a therapeutic output through specific ones of said plurality of contacts of said physical connector and (2) sense data indicative of a physiologic condition of a patient through said specific ones of said plurality of contacts of said physical connector; and
a communication module configured to communicate with an external communication device through said specific ones of said plurality of contacts of said physical connector;
wherein said communication through said communication module comprises a wakeup command and electronic data; and
wherein said implantable medical device is configured, upon receiving said wakeup command, to unlock functionality of said implantable medical device and to disable a functionality of said medical module to prevent interference between said communication using said electronic data and said data indicative of said physiologic condition.

12. The implantable medical device as in claim 11 wherein said specific ones of said plurality of contacts comprise a differential pair of contacts and wherein said communication module is configured to at least one of transmit and receive electronic communication differentially through said differential pair of contacts.

13. The implantable medical device as in claim 12 wherein said physical connector comprises a floating ground.

14. The implantable medical device as in claim 11 wherein said communication through said communication module comprises at least one of a command to control an operation of said implantable medical device and data relating to a condition of said implantable medical device.

15. The implantable medical device as in claim 14 wherein said communication through said communication module comprises a command to control an operation of said implantable medical device.

16. The implantable medical device as in claim 11 wherein when said implantable medical device has been implanted in a patient having a heart with periodic beats, said implantable medical device is configured, to disable said functionality of said medical module during a time between consecutive ones of said periodic beats; and
wherein said external communication device is configured to communicate only during said time between consecutive ones of said periodic beats.

17. The implantable medical device as in claim 11:
wherein said implantable medical device is configured to sense physiologic signals from said patient, said physiologic signals occurring in discrete time periods;
wherein said implantable medical device is configured such that communication through said communication module occurs only at a time other than said discrete time periods in which said physiologic signals are sensed by said implantable medical device.

18. The implantable medical device as in claim 11 wherein said external communication device is configured to be physically coupled to said plurality of contacts of said physical connector using at least one of a direct connection, a resistive connection and a capacitive connection.

19. The implantable medical device as in claim 11 wherein said implantable medical device further comprises a case containing said medical module and said communication module, and wherein said external communication device is configured to communicate with said communication module through said plurality of contacts of said physical connector and said case.

20. A method of operating an implantable medical device having a physical connector having a plurality of contacts, comprising the steps of:
performing at least one of:
delivering a therapeutic output through specific ones of said plurality of contacts of said physical connector; and
sensing data indicative of a physiologic condition of a patient through said specific ones of said plurality of contacts of said physical connector; and
electronically communicating with said implantable medical device through said specific ones of said plurality of contacts of said physical connector;
sending a wakeup command to said implantable medical to disable a functionality of said implantable medical device to prevent interference between said electronically communicating step and said sensing data indicative of a physiologic condition step.

21. The method as in claim 20 wherein said specific ones of said plurality of contacts of said physical connector comprise a differential pair of contacts and said communicating step comprises communicating differentially through said differential pair of contacts.

22. The method as in claim 21 wherein said communicating step comprises communicating with a floating ground.

23. The method as in claim 20 wherein said communicating step comprises at least one of a command to control an operation of said implantable medical device and data relating to a condition of said implantable medical device.

24. The method as in claim 23 wherein said communicating step comprises a command to control an operation of said implantable medical device.

25. The method as in claim 20 wherein said communicating step occurs only during a time between consecutive ones of periodic beats of a heart of said patient.

26. The method as in claim 20 wherein said communicating step occurs only at a time other than in discrete time periods in which physiologic signals are sensed by said implantable medical device.

27. The method as in claim 20 wherein said communicating step occurs with said external device being physically coupled to said plurality of contacts of said physical connector using at least one of a direct connection, a resistive connection and a capacitive connection.

28. The method as in claim 20 wherein said communicating step occurs through said plurality of contacts of said physical connector and said case.

* * * * *